United States Patent [19]
Dellagatta

[11] Patent Number: 5,954,675
[45] Date of Patent: Sep. 21, 1999

[54] METHOD OF ULTRASONIC THERAPY

[76] Inventor: Enrico Michael Dellagatta, c/o Maple Leaf Physical Therapy P.O. Box 663, Hammonton, N.J. 08037

[21] Appl. No.: 08/888,465

[22] Filed: Jul. 7, 1997

[51] Int. Cl.[6] .................................................. A61K 31/21
[52] U.S. Cl. .............................. 601/3; 604/890.1; 604/22
[58] Field of Search ........................... 601/2, 3; 600/437, 600/439; 607/50, 149, 152, 153; 604/890.1, 22

[56] References Cited

U.S. PATENT DOCUMENTS

| | | |
|---|---|---|
| 3,168,438 | 2/1965 | Halpern . |
| 3,272,834 | 9/1966 | Kraushaar et al. . |
| 4,329,338 | 5/1982 | Szegö et al. . |
| 4,795,638 | 1/1989 | Ayache et al. . |
| 4,990,340 | 2/1991 | Hidaka et al. . |
| 5,149,319 | 9/1992 | Unger . |
| 5,178,143 | 1/1993 | Kwak et al. . |
| 5,231,975 | 8/1993 | Bommannan et al. . |
| 5,302,172 | 4/1994 | Sage, Jr. et al. . |
| 5,383,848 | 1/1995 | Hillman et al. . |
| 5,405,366 | 4/1995 | Fox et al. . |
| 5,490,840 | 2/1996 | Uzgiris et al. . |
| 5,579,769 | 12/1996 | Yoshida et al. . |
| 5,618,275 | 4/1997 | Bock . |
| 5,636,632 | 6/1997 | Bommannan et al. . |
| 5,648,065 | 7/1997 | Meybeck et al. . |
| 5,733,572 | 3/1998 | Unger et al. . |
| 5,833,647 | 11/1998 | Edwards . |

OTHER PUBLICATIONS

C.J. Gean et al., "Cutaneous Responses to Topical Methyl Nicotinate in Black, Oriental, and Caucasian Subjects", *Arch. Dermatol Res.,* 28(2):95–98, Abstract from Medline database (1989).

L. Duteil et al., "Objective Assessment of Topical Corticosteroids and Non–Steroidal Anti–Inflammatory Drugs in Methyl–Nicotinate–Induced Skin Inflammation", *Clin. Exp. Dermatol.,* 15(3):195–199, Abstract from Medline database (May 1990).

P. Treffel et al., "Feasibility of Measuring the Bioavailability of Topical Ibuprofen in Commercial Formulations Using Drug Content in Epidermis and Methylnicotinate Skin Inflammation Assay", *Skin Pharmacol.,* 6:268–275, Abstract from Medline database (1993).

E. Tur et al., "Percutaneous Penetration of Methylnicotinate at Three Anatomic Sites: Evidence for an Appendageal Contribution to Transport?", *Skin Pharmacol.,* 4:230–234, 1991, Abstract from Medline database.

N.N. Byl, "The Use of Ultrasound as an Enhancer for Transcutaneous Drug Delivery: Phonophoresis", *Phys Ther.,* 75:539–553, Abstract from Medline database (Jun. 1995).

L.L. Tis, "The Role of Physical Modalities: Part II—Thermal Modalities", Chap. 6, pp. 65–71, *Rehabilitation of Injured Knee,* 2nd Ed. Mosby Yearbook Inc, (1995) (month unknown).

M.H. Cameron et al., "Relative Transmission of Ultrasound by Media Customarily used for Phonophoresis", *Physical Therapy,* 72(2):142–148, (Feb. 1992).

E. Smith et al., "Percutaneous Penetration Enhancers" pp. 7–8, CRC Press, Inc. (1995).

*Federal Register,* vol. 44, No. 234:69830, 68941–69842, (Dec. 1979).

*Federal Register,* vol. 48, No. 27:5867–5869, (Feb. 1983).

A. Hartley, "Ultrasound: A Monograph", pp. 1–32, (1991).

(List continued on next page.)

*Primary Examiner*—Scott M. Getzow
*Assistant Examiner*—Shawna J. Shaw
*Attorney, Agent, or Firm*—Howson and Howson

[57] ABSTRACT

Methyl nicotinate, when swabbed onto the skin prior to the application of therapeutic ultrasound, produces a surprising enhancement of the effect of the ultrasound treatment, making it possible to use less power and to apply the ultrasound over a shorter interval, and requiring no significant waiting time for the nicotinic acid ester to take effect.

11 Claims, 3 Drawing Sheets

OTHER PUBLICATIONS

G.P. Fulton et al., "The Mechanism of Action of Rubefacients", *J. of Investigative Dermatology,* 33(6):317–325 (Dec. 1959).

R.B. Stoughton et al., "Percutaneous Absorption of Nicotinic Acid and Derivatives", *J. Invest. Derm.,* 35:337–341 (1960).

E. Cronin et al., "Nicotinic Acid and Ethyl Nicotinate in Excised Human Skin", *Arch. Derm.,* 87:445–449 (1963).

A. Grollman et al., "Skin Irritants and Counter–Irritation", *Pharmacology,* $6^{th}$ Ed., Lea & Febiger, pp. 27–30 (1965).

"The Pharmacological Basis of Therapeutics, Textbook of Pharmacology, Toxicology, and Therapeutics for Physicians and Medical Students", Chap. 47, pp. 992, $8^{th}$ Ed., Dergamon Press, (1990).

J.C. Krantz et al., "The Pharmacologic Principles of Medical Practice, A Textbook on Pharmacology and Therapeutics for Medical Students, Physicians, and the Members of the Professions Allied to Medicine" $7^{th}$ Edition pp. 766–768 (1969).

K. Lange et al., "The Effect of Certain Hyperkinemics on the Blood Flow through the Skin" *J. ofInvest. Derm.,* pp. 263–269 (1949).

J.B. Peterson et al., "Responses of the Skin to Rubefacients" *J. ofInvest. Derm.,* 35:57–64 (1960).

Information Sheet on Methyl Nicotinate and Benzyl Nicotinate, *Pharmaceutical Chemicals,* Merck.

J.F. Lehmann et al., "Arthritis and Physical Medicine", *Therapeutic Heat and Cold,* pp. 316–317, Williams & Wilkins, Balitmore (1990).

J.B. Peterson et al., "A Clinical Evaluation of Nicotinate Rubtfacients" 82:495–500 (Oct. 1960).

"Modern Uses of Coirritation" *Pulse of Pharmacy,* 7(4)10:12 (1953) (Editorial).

"Methyl Nicotinate", *The Merck Index,* $10^{th}$ Edition, p. 873 (1983).

J.C. McElnay et al., "Phonophoresis of Methyl Nicotinate: A Preliminary Study to Elucidate the Mechanism of Action", *Pharm Res.* 10(12):1726–1731, Abstract from Medline database (Dec. 1993).

H.A. Benson et al., "Influence of Ultrasound on the Percutaneous Absorption of Nicotinate Esters", *Pharm. Res.,* 8(2):204–209, Abstract from Medline database (Feb. 1991).

G.K. Menon et al., "High–Frequency Sonophoresis: Permeation Pathways and Structural Basis for Enhanced Permeability", *Skin Pharmacol,* 7(3):130–139, Abstract from Medline database (1994).

C.S. Leopold et al., "Enhancing Effects of Lipophilic Vehicles on Skin Penetration of Methyl Nicotinate in Vivo", *J. Pharm Sci,* 84(2):195–198, Abstract from Medline database (Feb. 1995).

K.S. Ryatt et al., "Methodology to Measure the Transient Effect of Occlusion on Skin Penetration and Stratum Corneum Hydration in Vivo", *Br. J. Dermatol.,* 119(3):307–312, Abstract from Medline database (Sep. 1988).

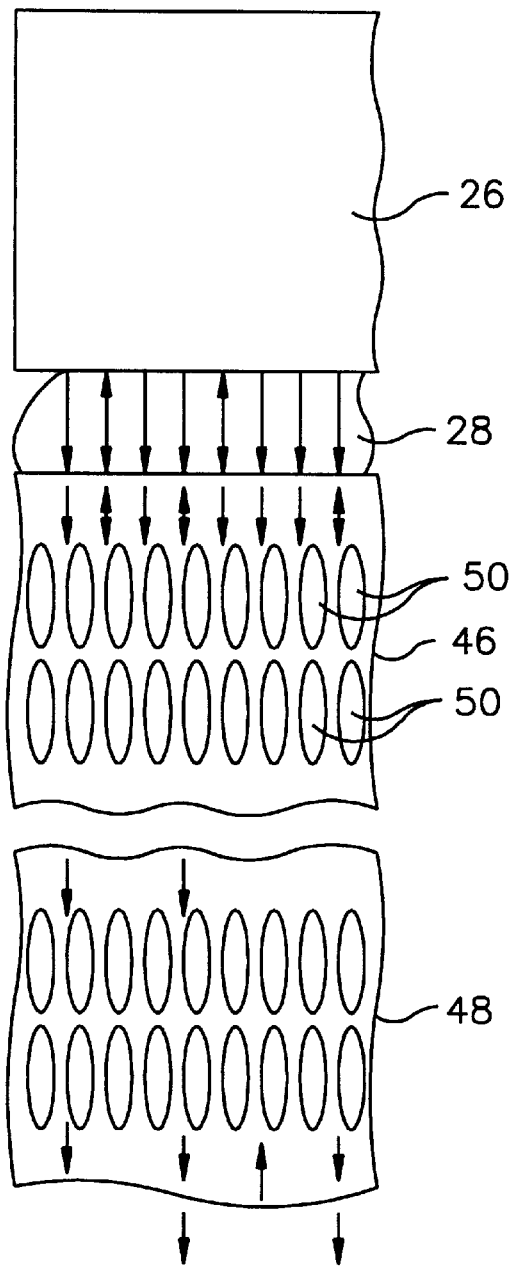 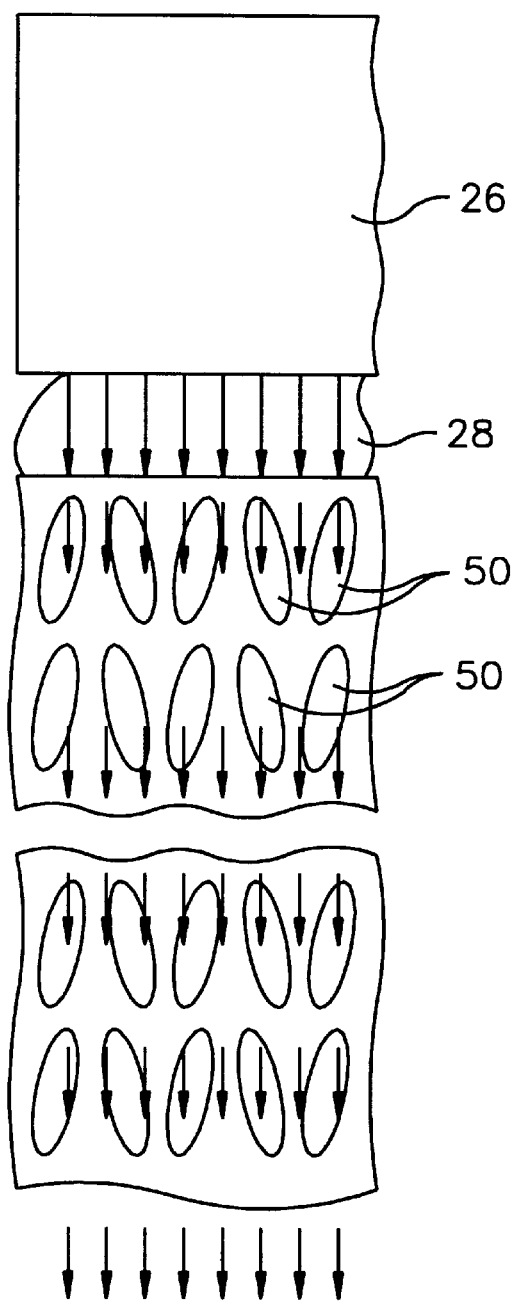
*Fig. 3*  *Fig. 4*

METHOD OF ULTRASONIC THERAPY

TECHNICAL FIELD

This invention relates generally to the field of health care and physical therapy. More particularly, the invention relates to a method of ultrasonic therapy in which, prior to the application of ultrasonic energy, the site at which the ultrasonic transducer is to come into contact with the patient's skin is treated topically with a formulation which enhances the therapeutic effects of ultrasonic energy.

BACKGROUND OF THE INVENTION

Physical therapists have long utilized therapeutic ultrasound because of its thermal and mechanical effects on tissue. Ultrasound (sound at a frequency greater than approximately 20 KHz.) can be produced by applying an alternating electrical current, at the desired frequency, to a transducer incorporating a piezoelectric crystal. The current causes the shape of the crystal to oscillate between a resting state and a different state, thereby producing a sonic wave. The sonic wave can be continuous or pulsed, depending on how the transducer is driven.

Typical indications calling for ultrasonic therapy include tendinitis, bursitis, carpal tunnel syndrome, neck pain and lower back pain. Continuous ultrasound is typically used when thermal effects are desired, for example to reduce muscle spasm. On the other hand, pulsed ultrasound is often preferred for treatment where heat exacerbates pain in the patient, or when only non-thermal, mechanical effects of ultrasound, e.g. enhancement of tissue regeneration, are desired.

In transdermal ultrasonic therapy, a coupling gel is used between the transducer and the patient's skin to eliminate any layer of air, and thereby reduce reflections resulting from the difference in the acoustical impedances of air and the transducer. Typical coupling agents are mineral oil, glycerin, propylene glycol, water and water-based gels.

Ultrasonic therapy is widely used, but for effective treatment, it has generally been necessary to apply ultrasonic energy either at a high intensity or for long intervals of time, or both. An important object of this invention is to provide a method for carrying out ultrasonic therapy in which the transmission of ultrasonic energy through the patient's skin is enhanced.

SUMMARY OF THE INVENTION

In accordance with the invention, a solution of a nicotinic acid ester is applied to a defined area of a patient's skin overlying a tissue lesion to be treated. The nicotinic acid ester is applied to the defined area of the patient's skin by means of a swab pre-saturated with a mixture including the nicotinic acid ester and an alcohol. Following the application of the nicotinic acid ester, ultrasonic energy is applied to the internal tissue lesion by a transducer in contact with the defined area to which the nicotinic acid ester was applied. It has been found that the nicotinic acid ester and the ultrasonic energy, acting together, produce a surprising effect as exhibited by measurements of cutaneous circulation (perfusion). The application of the nicotinic acid ester to the skin apparently produces a hydration of the stratum corneum (the surface layer of the patient's epidermis), which, prior to hydration, has a relatively high acoustic impedance compared to the that of the underlying epidermal and dermal layers and the overlying coupling agent. Hydration of the stratum corneum causes its acoustic impedance to approach that of the underlying layers and the coupling agent. The modification of the impedance of the stratum corneum reduces the reflection coefficients at the interface between the stratum corneum and the underlying granular layer of the epidermis and at the interface between the coupling agent and the stratum corneum, thereby improving the transmission of ultrasonic energy to the internal tissue lesion.

A preferred nicotinic acid ester is methyl nicotinate, applied in a solution containing approximately 1% (wt.) methyl nicotinate, approximately 10%–20% (wt.) isopropyl alcohol and water. The frequency of the ultrasonic energy is preferably in the range of approximately 700 KHz. to 3500 KHz.

Other objects, advantages and details of the invention will be apparent from the following detailed description, when read in conjunction with the drawings.

BRIEF DESCRIPTION OF THE DRAWINGS

FIG. 3 is a schematic cross section showing an ultrasonic transducer, a layer of coupling agent, and the stratum corneum of the patient's epidermis, the stratum corneum being untreated, as in the prior art; and FIG. 4 is a schematic cross section showing an ultrasonic transducer, a layer of coupling agent, and the stratum corneum of the patient's epidermis, the stratum corneum being treated with a nicotinic acid ester in accordance with the invention.

DETAILED DESCRIPTION

Figure 1:
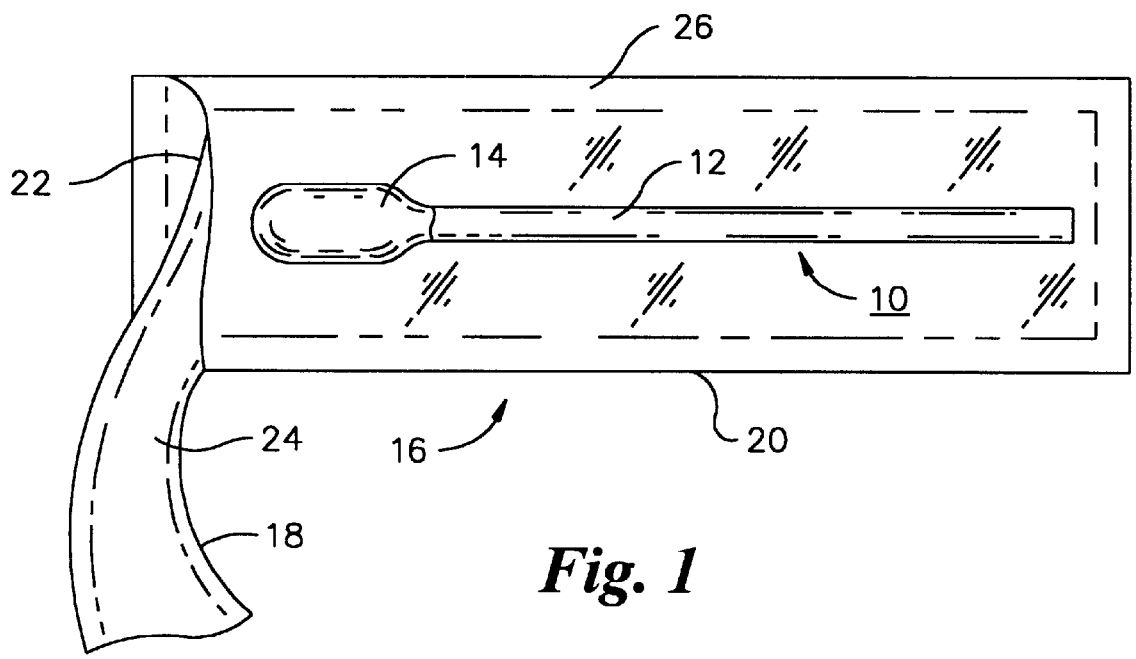
FIG. 1 is an elevational view of a swab stick for applying the nicotinic acid ester solution according to the invention, showing the package containing the swab stick opened and partially broken away.

Ultrasonic therapy in accordance with the invention is preferably carried out by utilizing a pre-packaged methyl nicotinate swab stick 10 as shown in FIG. 1, the stick comprising a stiff, extruded tube 12 of plastics material, e.g. polyethylene, having a quantity of fiber affixed at one end in the form of a dense bulb 14, saturated with a solution of a nicotinic acid ester, preferably a solution consisting of approximately 1% (wt.) methyl nicotinate, approximately 10% (wt.) isopropyl alcohol, and water. The fiber can be a natural fiber such as cotton, a synthetic cotton-like material such as rayon, or a blend of natural and synthetic fibers.

The pre-saturated swab stick 10 is supplied enclosed in a package 16 made from two sheets 18 and 20, each consisting of a layer of coated paper and a layer of aluminum foil, the paper layer of sheet 18 being indicated at 22 and the foil layer of sheet 18 being indicated at 24. The two sheets are adhesively secured to each other along a border 26 to form an air and liquid-tight enclosure for the swab stick.

Isopropyl alcohol is preferably present in the methyl nicotinate solution because of its antiseptic properties, to increase the shelf life of the swab stick, to aid in cleansing the surface of the skin, and to enhance the penetration of the methyl nicotinate into the skin by fluidizing the lipid barriers in the skin. To be effective, the amount of isopropyl alcohol in the solution should be at least 10% by weight based on the total weight of the solution.

Prior to treatment with ultrasonic energy, a defined area of the patient's skin is swabbed with the methyl nicotinate solution. The defined area overlies the tissue lesion being treated. Immediately after the area is swabbed with the methyl nicotinate solution, a coupling agent is applied to the same area and an ultrasonic transducer is brought into contact with the defined area through the coupling agent, and operated.

Figure 2:
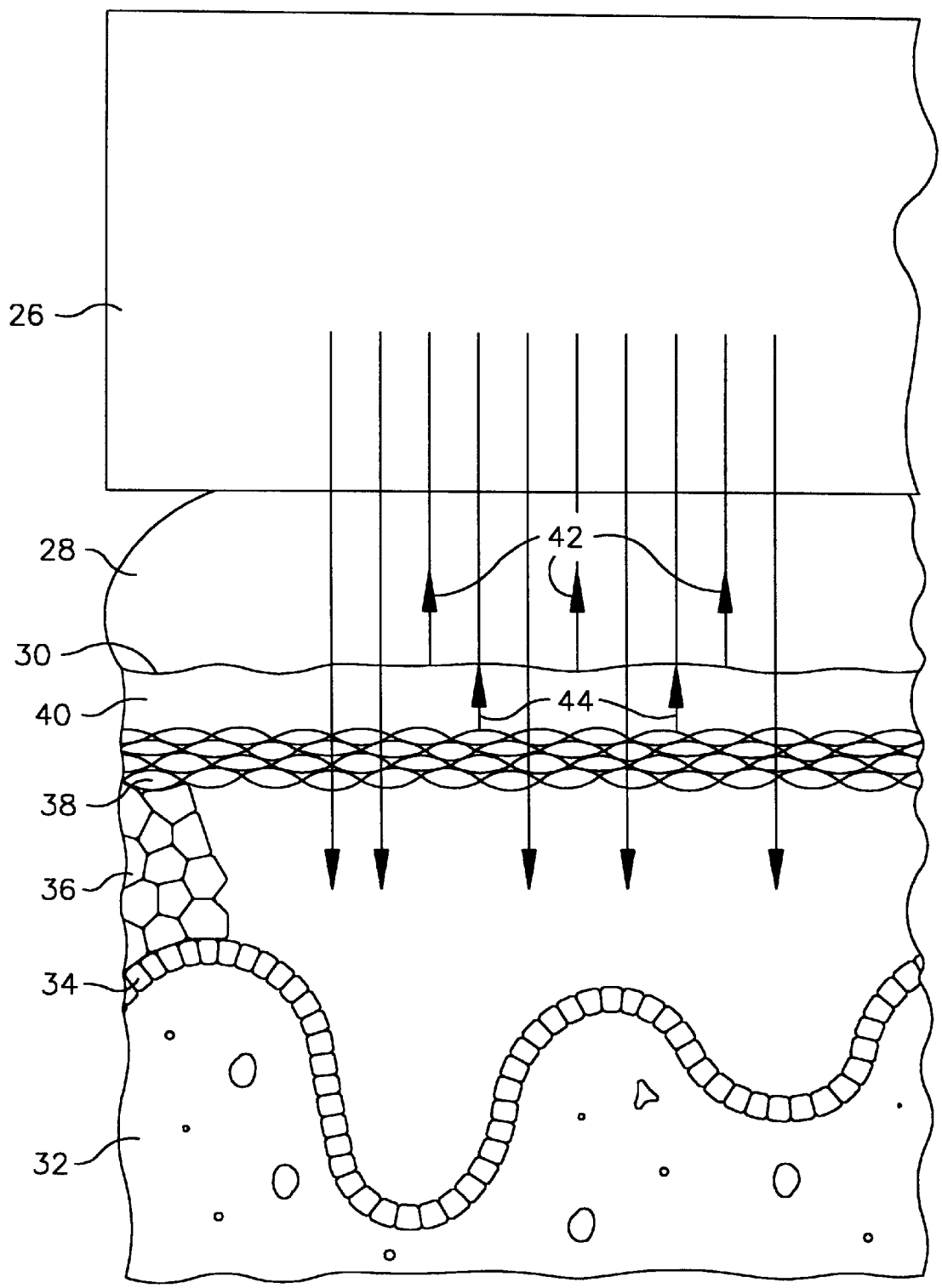
FIG. 2 is a schematic cross section showing an ultrasonic transducer, a layer of coupling agent, the patient's epidermis, and part of the dermis, with the direction of the transmitted ultrasound and its reflections being shown by arrows.

When therapeutic ultrasound is applied to a patient, it is usually in the frequency range from 870 kHz. to 3.3 MHz., at an intensity up to about 3 W/cm$^2$, and is applied by means of a piezoelectric transducer such as transducer 26, shown schematically in FIG. 2. The ultrasonic energy is transmitted through a thin layer 28 of a coupling agent, typically a water-based gel to the surface 30 of the skin of the patient. The skin consists of a dermis 32 and an epidennis, the latter comprising four principal layers: the basilar membrane or basal layer 34, the stratum spinosun, or spinous layer 36, the stratum granulosum or granular layer 38, and the stratum corneum or horny layer 40.

The stratum corneum 40 is typically about 10 $\mu$M thick, and consists of keratinized cells. Its water content is normally less than that of the underlying granular, spinous and basal layers, and consequently its acoustic impedance, the product of its density and the velocity of sound through it, is greater than that of the underlying layers. The density $\rho$ of an acoustic medium has the dimensions g/cm$^3$, and c, the velocity of sound in the medium, has the dimensions cm/sec. Thus, the acoustic impedance $\rho$c has the dimensions $$\frac{g}{cm^2 \cdot sec}.$$

The power reflection coefficient R at an interface between two media having acoustic impedances $\rho_1 c_1$ and $\rho_2 c_2$ is given by the equation:

$$R = \left[\frac{\rho_1 c_1 - \rho_2 c_2}{\rho_1 c_1 + \rho_2 c_2}\right]^2$$

Thus, reflection is minimized as the acoustic impedances of the two media approach each other.

While I do not wish to be bound by any particular theory, I believe that the topical application of the nicotinic acid ester solution to the patient prior to the application of ultrasonic energy increases cutaneous circulation by stimulation of the axons innervating the small papillary and subpapillary arterioles, and, as a result, causes hydration of the stratum corneum. and in the stratum comeum.

The hydration of the stratum corneum occurs very rapidly as a result of the application of the nicotinic acid ester. Hydration decreases the acoustic impedance of the stratum corneum 40 so that it approaches that of the underlying epidermal layers 38, 36 and 34, the dermal layer 32, and the coupling agent 28. Consequently, reflections 42 of the ultrasonic energy from the interface between the coupling agent 28 and the stratum corneum 40 are reduced. Likewise reflections 44 at the interface between the stratum corneum 40 and the granular layer 38 are reduced. With the reduction in reflected energy, more energy is transmitted through the epidermis and dermis to the lesion being treated. The hydration of the stratum corneum also reduces the ultrasonic attenuation of the stratum corneum.

The application of the nicotinic acid ester to the stratum corneum, both by itself, and in combination with the applied ultrasonic energy, also fluidizes the lipid interface between the keratinized proteins in the stratum corneum, and alters the spacing between the proteins. The fluidization of the lipid interface and the alteration of the spacing between proteins, also contribute to the decrease in the acoustic impedance of the stratum corneum and to the decrease in its attenuation of the ultrasonic energy.

As shown in FIG. 3, the stratum corneum comprises multiple layers (two of which are shown at 46 and 48) of keratinized proteins 50. These proteins are normally closely spaced from one another and separated by a lipid interface. Ultrasonic energy applied by a transducer 26 through a coupling agent layer 28 is both reflected and absorbed by the layers of the stratum corneum. The upwardly directed arrows signify reflected energy.

As shown in FIG. 4, which depicts the stratum corneum after having been treated by the application of a nicotinic acid ester, the lipid interface between the proteins becomes fluidized and the spacing of the proteins is altered. This fluidization of the lipid interface and the alteration of the spacing of the proteins also contributes to the decrease of the acoustic impedance of the stratum corneum and to the decrease in its attenuation coefficient. In FIG. 4, the arrows indicate that more of the ultrasonic energy is directed through the stratum corneum, and that less energy is absorbed or reflected.

In contrast, conventional gels and other coupling agents produce little hydration of the stratum corneum even after ultrasound is applied for five minutes, and have little effect on the acoustic impedance and attenuation coefficient of the stratum corneum.

The effectiveness of methyl nicotinate and ultrasonic treatment in combination was demonstrated by a study carried out on ten healthy volunteers, ranging in age from 19 to 57. Individuals having a history of vascular or skin pathology were excluded from the study.

A Moor Instruments, Inc. LDI laser Doppler image scanner was used to assess cutaneous circulation. Laser light was directed toward the skin through a glass optical fiber. A fiber-optic system was used to collect a portion of the backscattered light and direct it to a photodetector. Movement of red blood cells caused a Doppler shift in the frequency of the backscattered light. From the frequency shift, information concerning the quantity and velocity of the red blood cells was determined.

The subjects were positioned supine on a stationary table with hip and knee flexion maintained, lending support to the lower back. The procedure was carried out in two phases. With a subject positioned on the table, a baseline scan was taken of a 2×3 inch rectangular area on the anterior shoulder prior to the application of ultrasound. Ultrasound was administered at a frequency of 3.3 MHz. and a power level of 1.5 watts/cm$^2$ for five minutes. A repeat scan was performed immediately following treatment. On another, non-consecutive day, each subject was returned for the same procedure, on the same shoulder, preceded by a preparatory application of a 1% solution of methyl nicotinate in water.

The numbers in the following table, which represent "perfusion," correspond to the Doppler shift in the laser light as measured by the laser Doppler image scanner, and are proportional to the speed and concentration of red blood cells in the volume of tissue in which the measurement took place. The laser Doppler image scanner measures perfusion to a depth of approximately 1 mm.

|         | Pre treatment        |        | Post-treatment       |                    |                   |                  |
| ------- | -------------------- | ------ | -------------------- | ------------------ | ----------------- | ---------------- |
| Subject | Day 1 (Control)      | Day 2  | Day 1 (Control)      | Day 2 (Swabbed)    | Control change    | Change Day 2     |
| 1       | 49.00                | 42.00  | 63.00                | 390.00             | 14.00             | 348.00           |
| 2       | 71.00                | 35.00  | 143.00               | 251.00             | 72.00             | 216.00           |
| 3       | 33.00                | 21.00  | 245.00               | 220.00             | 212.00            | 199.00           |
| 4       | 78.00                | 56.00  | 70.00                | 482.00             | −8.00             | 426.00           |
| 5       | 38.00                | 71.00  | 143.00               | 359.00             | 105.00            | 288.00           |
| 6       | 38.00                | 38.00  | 105.00               | 397.00             | 67.00             | 359.00           |
| 7       | 31.00                | 29.00  | 31.00                | 211.00             | 0.00              | 182.00           |
| 8       | 38.00                | 29.00  | 55.00                | 283.00             | 17.00             | 254.00           |
| 9       | 42.00                | 46.00  | 177.00               | 245.00             | 135.00            | 199.00           |
| 10      | 50.00                | 40.00  | 55.00                | 187.00             | 5.00              | 147.00           |
| MEAN    | 46.80                | 41.00  | 108.70               | 303.00             | 61.90             | 261.80           |
| STD     | 15.07                | 13.73  | 64.03                | 93.20              | 67.92             | 86.09            |

The change in perfusion from pre-treatment to post-treatment is tabulated or each subject. The mean change in perfuision was 61.9 for the control, and 261.8 when the shoulders were swabbed with methyl nicotinate solution prior to application of the ultrasound. A paired t-test shows that there is a significant difference between the change in perfusion for the control and the change in perfusion for effected by methyl nicotinate treatment. (t=4.971, df=9, p=0.001). The study basically indicates that the combination of methyl nicotinate and ultrasound produces a much greater perfusion change than is accomplished by ultrasound alone.

The methyl nicotinate solution has also been found to be more effective than a hot pack as a preliminary to ultrasound treatment. In a study of hot pack application followed by ultrasound treatment, the mean change in perfusion was 151.20, showing that the hot pack followed by ultrasound was more effective than ultrasound alone, but substantially less effective than methyl nicotinate followed by ultrasound, the latter producing a mean change in perfusion of 261.80.

Methyl nicotinate solution can be applied, preferably by the use of a pre-packaged swab, as shown in FIG. 1, to increase the effectiveness of transdermal ultrasound, in many different situations. Specific indications include carpal tunnel syndrome, tennis elbow, medial epicondylitis (golfer's's elbow), plantar fasciitis, DeQuervain's tenosynovitis, patellar tendinitis, Achilles tendinitis, rotator cuff syndrome, low back pain, myofascial trigger points, trigger finger, hamstring tendinitis, olecranon bursitis, iliotibial-band friction syndrome, calcaneal bursitis and biceps brachii tendinitis.

The following example illustrates a specific sequence of steps carried out in a treatment in accordance with the invention.

EXAMPLE

The swab was presaturated with a solution consisting of 1% methyl nicotinate, 10% isopropyl alcohol, and 89% water.

The packaged swab was opened by tearing the package in such a way that the user's fingers could grasp the extruded tube 12 without contacting the bulb 14. This prevents the active ingredient from coming into contact with the hands. A predefined 2 inch×3 inch area of the patient's shoulder was swabbed with a up and down and side to side motion. A commercially available coupling agent, AQUASONIC 100 ultrasound transmission gel, available from Parker Laboratories, Inc. of Orange, N.J., U.S.A., was then applied to the same area, and immediately thereafter, an ultrasonic transducer was brought into contact with the area. Ultrasound at 3.3 MHz. was applied for five minutes at a level of 1.5 watts/cm$^2$.

This treatment was applied to a patient with acute rotator cuff strain. As a result of a short series of treatments, the patient experienced decreased pain, increased range of motion and increased tension development.

Hyperemia, the overt measure of increased local circulation, subsides in two to three hours. Localized circulation increases the mobility of intracellular fluids to the extracellular spaces and thus accelerates metabolism. The accelerated metabolism facilitates mitotic replication of somatic cells and ultimately tissue repair. This is accomplished because the increased circulation provides the oxygenated blood necessary to catalyze the oxidative phosphorylation of ATP prerequisite to cellular repair.

The application of the methyl nicotinate solution followed by 5 minutes of ultrasound (3.3 MHZ) elevates the surface blood flow 4 to 8 times above the pre-application level. It also increases the moisture content of the skin. These effects occur within about 2 minutes after application. They last at optimum level for approximately 90 minutes and then decrease gradually over another 90 minute interval.

Methyl nicotinate is not recommended for use in facial area, and it is particularly important to avoid contact with the eyes. It is not intended for use with diagnostic ultrasound.

The procedure has applications in sports medicine. For example methyl nicotinate application followed by therapeutic ultrasound can be used to increase superficial perfusion in the pitching shoulder of a baseball pitcher prior to a game or workout. The same treatment can also be applied to the shoulders, back or knees of an ice hockey player, to the hamstring area of a football player or to the shoulders or knees of a weight lifter.

Among the advantages of the use of a nicotinic acid ester as a preliminary treatment is the fact that it acts very rapidly. Since it reaches its full effect within about two minutes, and part of that time is taken up by the application of the coupling agent, there is no need for the therapist to wait for the methyl nicotinate to take effect. Substantially immediately after the desired area of the skin is swabbed with the nicotinic acid ester, the coupling agent is applied, and the ultrasonic transducer can be applied to the patient's skin and operated.

Modifications can be made in the solution. For example, the concentration of methyl nicotinate can be varied from 0.5% to 5%. The isopropyl alcohol content can be eliminated altogether, but, if present, should be in the range from about 10% to 50%. Other alcohols, for example, ethyl alcohol, can be used instead of isopropyl alcohol. Likewise, various other additives can be included in the solution containing methyl nicotinate, and other modifications can be made to the composition of the methyl nicotinate solution and the method of its application without departing from the scope of the invention as defined in the following claims.

I claim:

1. A method of ultrasonic therapy comprising the steps of:
   (a) preparing a patient by applying, to a defined area of the patient's skin, a solution of a nicotinic acid ester; and
   (b) transmitting ultrasonic energy to an internal tissue lesion underlying said defined area by means of a transducer in contact with said defined area;
   in which the frequency of the ultrasonic energy is in the range of approximately 700 KHz. to 3500 KHz.

2. A method according to claim 1, in which the nicotinic acid ester solution comprises approximately 0.5 to 5% (wt.) methyl nicotinate together with alcohol and water.

3. The method of claim 2, in which the step of preparing the patient by applying a solution of nicotinic acid ester is followed by, and the step of transmitting ultrasonic energy is preceded by, the step of applying a coupling agent to said defined area of the patient's skin.

4. A method according to claim 2, in which the solution of a nicotinic acid ester is applied to the defined area of the patient's skin by means of a swab pre-saturated with a solution of a nicotinic acid ester.

5. A method according to claim 2, in which the step of transmitting ultrasonic energy substantially immediately follows the step of applying a solution of a nicotinic acid ester.

6. A method according to claim 2, in which the solution contains approximately 1% (wt.) methyl nicotinate.

7. A method according to claim 2, in which the alcohol is isopropyl alcohol, present in an amount constituting approximately 10% to 50% of the weight of the solution.

8. A method according to claim 2, in which the solution contains approximately 1% (wt.) methyl nicotinate and in which the alcohol is isopropyl alcohol, present in an amount constituting approximately 10% to 50% of the weight of the solution.

9. A method according to claim 1, in which the step of preparing the patient is followed by, and the step of transmitting ultrasonic energy is preceded by, the step of applying a coupling agent to said defined area of the patient's skin.

10. A method according to claim 1, in which the solution of a nicotinic acid ester is applied to the defined area of the patient's skin by means of a swab pre-saturated with a solution of a nicotinic acid ester.

11. A method according to claim 1, in which the step of transmitting ultrasonic energy substantially immediately follows the step of applying a solution of a nicotinic acid ester.

* * * * *